United States Patent
Nouwen et al.

(10) Patent No.: US 6,563,004 B2
(45) Date of Patent: May 13, 2003

(54) PROCESS FOR PREPARING MONOISOPROPYLAMINE

(75) Inventors: Jan Nouwen, Lorsch (DE); Stefan Käshammer, Schifferstadt (DE); Arthur Höhn, Kirchheim (DE); Frank Funke, Frankenthal (DE); Johann-Peter Melder, Böhl-Iggelheim (DE); Frank Gutschoven, Antwerpen (BE); Philip Buskens, Hoogstraten (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/729,461

(22) Filed: Dec. 5, 2000

(65) Prior Publication Data

US 2001/0003137 A1 Jun. 7, 2001

(30) Foreign Application Priority Data

Dec. 6, 1999 (DE) .......................... 199 58 701

(51) Int. Cl.⁷ ............................................ C07C 209/26
(52) U.S. Cl. ...................................................... 564/472
(58) Field of Search ......................................... 564/472

(56) References Cited

U.S. PATENT DOCUMENTS

| | | | |
|---|---|---|---|
| 4,014,933 A | * 3/1977 | Boettger et al. | 260/563 R |
| 4,234,727 A | 11/1980 | Toussaint et al. | 544/178 |
| 5,002,922 A | 3/1991 | Irgang | |
| 5,166,433 A | * 11/1992 | Irgang et al. | 564/106 |
| 5,530,127 A | 6/1996 | Reif et al. | 544/106 |
| 5,608,113 A | 3/1997 | Becker et al. | 564/480 |
| 5,952,529 A | 9/1999 | Chang et al. | 564/480 |
| 6,057,442 A | 5/2000 | Wulff-Doring et al. | 544/106 |
| 6,417,353 B1 | 7/2002 | Funke et al. | 540/450 |
| 2001/0003136 A1 | 6/2001 | Nouwen et al. | 564/396 |

FOREIGN PATENT DOCUMENTS

| | | |
|---|---|---|
| DE | 1 817 691 | 6/1970 |
| DE | 1953 263 | 2/1972 |
| DE | 1 793 220 | 3/1972 |
| DE | 1 543 354 | 4/1972 |
| DE | 2 219 475 | 11/1973 |
| DE | 28 38 184 | 3/1980 |
| DE | 198 59776 | 6/2000 |
| DE | 199 10 960 | 9/2000 |
| EP | 284 398 | 9/1988 |
| EP | 382 049 | 8/1990 |
| EP | 514 692 | 11/1992 |
| EP | 696 572 | 2/1996 |
| EP | 0 697 395 | 2/1996 |
| EP | 0 905 122 | 3/1999 |
| EP | 963 975 | 12/1999 |
| EP | 1 035 106 | 9/2000 |
| GB | 1190435 | 5/1970 |
| GB | 1 218 454 | 1/1971 |
| GB | 1 421 278 | 1/1976 |

OTHER PUBLICATIONS

Abst. 71:38326=DE 18 03 083, 1970.
Abst. 46450170=DE 18 17 691, 1970.
Abst. 74:76004=FR 1 590 871, 1970.
Abst. 39 095170=DE 18 03 083, 1970.
Abst. 111:161414=HU 47 456, 1989.
Derwent Abst. 97 385916=CN 11 10 629, 1995.
Abst. 76368/70=DL 75 086, 1968.

* cited by examiner

*Primary Examiner*—Brian Davis
(74) *Attorney, Agent, or Firm*—Keil & Weinkauf

(57) ABSTRACT

Monoisopropylamine is prepared by reacting acetone with ammonia and with hydrogen at elevated temperature and elevated pressure in the presence of a catalyst, wherein the catalytically active mass of the catalyst comprises, after its preparation and before the treatment with hydrogen, from 20 to 90% by weight of aluminum oxide ($Al_2O_3$), zirconium dioxide ($ZrO_2$), titanium dioxide ($TiO_2$) and/or silicon dioxide ($SiO_2$), from 1 to 70% by weight of oxygen-containing compounds of copper, calculated as CuO, from 1 to 70% by weight of oxygen-containing compounds of nickel, calculated as NiO, and from 1 to 70% by weight of oxygen-containing compounds of cobalt, calculated as CoO.

9 Claims, No Drawings

PROCESS FOR PREPARING MONOISOPROPYLAMINE

The present invention relates to a process for preparing monoisopropylamine (MIPA; $(CH_3)_2CHNH_2$) by reacting acetone at elevated temperature and elevated pressure with ammonia and with hydrogen in the presence of a catalyst.

MIPA is an important organic intermediate which is required inter alia as precursor for preparing crop protection agents.

MIPA is prepared industrially by aminating hydrogenation of isopropanol or acetone with ammonia using catalysts.

DE-A-1 543 354 discloses the synthesis of MIPA by aminating hydrogenation of acetone in the presence of cobalt catalysts.

DT-A-1803 083, DT-A-1817 691, FR-A-159 0871, DE-A-18 03 083 and HU-A-47456 describe the preparation of MIPA by aminating hydrogenation of acetone in the presence of catalysts of the Raney nickel type.

DL-A-75086, DE-A-17 93 220, GB-A-1218 454, CN-A-1130 621, CS-A-185 962 and CS-A-239 445 relate to the preparation of MIPA by aminating hydrogenation of acetone in the presence of nickel/aluminum oxide catalysts.

DE-A-22 19 475 (loc. cit., Examples 10 to 12) describes the synthesis of MIPA from acetone in the presence of a nickel/chromium/kieselguhr catalyst.

EP-A-284 398 and CN-A-111 0629 relate to nickel catalysts doped with Ru or with Cr and Cu for preparing MIPA from acetone.

The earlier German application no. 19910960.5 of Mar. 12, 1999 discloses catalysts consisting of nickel, copper, molybdenum and zirconium dioxides for preparing MIPA by catalytic amination of acetone in the presence of hydrogen (loc. cit., Example 1). The selectivity of this conversion is only 82.3 to 95.2%.

The earlier German application no. 19859776.2 of Dec. 23, 1998 describes the preparation of MIPA from acetone and ammonia using a catalyst comprising copper and $TiO_2$ (loc. cit., Example 5).

The disadvantage of prior art processes is that the selectivities and yields in the aminating hydrogenation of acetone are too low. Even on use of a large molar excess of ammonia relative to acetone, as, for example, in GB-A-1218 454, Example 4, the maximum selectivity based on acetone is only 96.24% by weight.

EP-A-514 692 discloses catalysts containing copper, nickel and/or cobalt, zirconium oxide and/or aluminum oxide for the catalytic amination of alcohols in the gas phase with ammonia or primary amines and hydrogen.

EP-A-382 049 discloses catalysts which comprise oxygen-containing zirconium, copper, cobalt and nickel compounds, and processes for the hydrogenating amination of alcohols or carbonyl compounds. The preferred zirconium oxide content in these catalysts is from 70 to 80% by weight (loc. cit.: page 2, last paragraph; page 3, $3^{rd}$ paragraph; Examples).

DE-A-19 53 263 discloses the use of Co-, Ni- and Cu-containing catalysts with $Al_2O_3$ or $SiO_2$ as carrier material for preparing amines from alcohols.

The earlier European application no. 99111282.2 of Jun. 10, 1999 relates to a process for preparing amines by reacting primary or secondary alcohols with nitrogen compounds in the presence of catalysts comprising zirconium dioxide, copper, nickel and cobalt.

It is an object of the present invention to remedy the disadvantages of the prior art and improve the economics of previous processes for preparing MIPA by aminating hydrogenation of acetone with ammonia. It was intended to find catalysts which can be obtained easily or can be prepared in a technically simple manner and which permit the aminating hydrogenation of acetone to give MIPA to be carried out with a high acetone conversion, in particular acetone conversions of from 90 to 100%, high yield, high selectivity, in particular selectivities of from 96.5 to 100% (based on acetone), and high catalyst service life with, at the same time, high mechanical stability of the catalyst shaped article. The catalysts ought accordingly to have a high activity and a high chemical stability under the reaction conditions, and achieve the above object even on use of an only small molar excess of ammonia relative to acetone.

We have found that this object is achieved by a process for preparing monoisopropylamine (MIPA) by reacting acetone with ammonia and with hydrogen at elevated temperature and elevated pressure in the presence of a catalyst, wherein the catalytically active mass of the catalyst comprises, after its preparation and before the treatment with hydrogen, from 20 to 90% by weight of aluminum oxide ($Al_2O_3$), zirconium dioxide ($ZrO_2$), titanium dioxide ($TiO_2$) and/or silicon dioxide ($SiO_2$), from 1 to 70% by weight of oxygen-containing compounds of copper, calculated as CuO, from 1 to 70% by weight of oxygen-containing compounds of nickel, calculated as NiO, and from 1 to 70% by weight of oxygen-containing compounds of cobalt, calculated as CoO.

In general, the catalysts employed in the process according to the invention are preferably in the form of catalysts which consist only of catalytically active mass and, where appropriate, a shaping auxiliary (such as, for example, graphite or stearic acid) if the catalyst is employed as shaped articles, that is to say contain no other catalytically inactive additives.

The catalytically active mass can be introduced after grinding as powder or as chips into the reaction vessel or, preferably, after grinding, mixing with molding auxiliaries, shaping and annealing, introduced as catalyst shaped articles—for example as tablets, beads, rings, extrudates (for example strands)—into the reactor.

The concentration data (in % by weight) of the components of the catalyst are in each case based—unless stated otherwise—on the catalytically active mass of the prepared catalyst after its last heat treatment and before the treatment with hydrogen.

The catalytically active mass of the catalyst after its last heat treatment and before the treatment with hydrogen is defined as the total of the masses of the catalytically active ingredients and the carrier materials and essentially comprises oxygen-containing compounds of aluminum, zirconium, titanium and/or silicon, oxygen-containing compounds of copper, oxygen-containing compounds of nickel and oxygen-containing compounds of cobalt.

The total of the abovementioned catalytically active ingredients and of the abovementioned carrier materials in the catalytically active mass, calculated as $Al_2O_3$, $ZrO_2$, $TiO_2$, $SiO_2$, CuO, NiO and CoO, is normally from 70 to 100% by weight, preferably from 80 to 100% by weight, particularly preferably from 90 to 100% by weight, in particular from 95 to 100% by weight, very especially 100% by weight.

The catalytically active mass of the catalysts employed in the process according to the invention may further comprise one or more elements (oxidation state 0) or their inorganic or organic compounds selected from groups I A to VI A and I B to VII B and VIII of the Periodic Table.

Examples of such elements and their compounds are:

transition metals such as Mn or manganese oxides, Re or rhenium oxides, Cr or chromium oxides, Mo or molybdenum oxides, W or tungsten oxides, Ta or tantalum oxides, Nb or niobium oxides or niobium oxalate, V or vanadium oxides or vanadyl pyrophosphate, zinc or zinc oxides, silver or silver oxides, lanthanides such as Ce or $CeO_2$ or Pr or $Pr_2O_3$, alkali metal oxides such as $Na_2O$, alkali metal carbonates such as $Na_2CO_3$ and $K_2CO_3$, alkaline earth metal oxides such as SrO, alkaline earth metal carbonates such as $MgCO_3$, $CaCO_3$, $BaCO_3$, phosphoric anhydrides and boron oxide ($B_2O_3$).

The catalytically active mass of the catalysts employed in the process according to the invention comprises, after preparation thereof and before the treatment with hydrogen, from 20 to 90% by weight, preferably from 20 to 85% by weight, particularly preferably from 40 to 85% by weight, very particularly preferably from 50 to 85% by weight, of aluminum oxide ($Al_2O_3$), zirconium dioxide ($ZrO_2$), titanium dioxide ($TiO_2$) and/or silicon dioxide ($SiO_2$), from 1 to 70% by weight, preferably from 1 to 40% by weight, particularly preferably from 1 to 25% by weight, very particularly preferably from 1 to 15% by weight, of oxygen-containing compounds of copper, calculated as CuO, from 1 to 70% by weight, preferably from 5 to 50% by weight, particularly preferably from 5 to 40% by weight, very particularly preferably from 5 to 25% by weight, of oxygen-containing compounds of nickel, calculated as NiO, and from 1 to 70% by weight, preferably from 5 to 50% by weight, particularly preferably from 5 to 40% by weight, very particularly preferably from 5 to 25% by weight, of oxygen-containing compounds of cobalt, calculated as CoO.

The catalytically active mass of very particularly preferably employed catalysts comprises, after preparation thereof and before the treatment with hydrogen, from 50 to 85% by weight of aluminum oxide ($Al_2O_3$) and/or silicon dioxide ($SiO_2$), from 1 to 15% by weight of oxygen-containing compounds of copper, calculated as CuO, from 5 to 25% by weight of oxygen-containing compounds of nickel, calculated as NiO, and from 5 to 25% by weight of oxygen-containing compounds of cobalt, calculated as CoO.

In the catalysts preferably employed in the process according to the invention, the ratio by weight of cobalt to nickel, in each case calculated as metal, is from 4:1 to 1:4, particularly preferably from 2:1 to 1:2.

In addition, in catalysts preferably employed in the process according to the invention, the ratio by weight of (cobalt and nickel) to copper, in each case calculated as metal, is from 3:1 to 20:1, particularly preferably from 3:1 to 10:1.

Catalysts preferably employed in the process according to the invention contain no catalytically active amounts of V, Nb, Ta, Cr, Mo, W, Mn and/or Re and/or their inorganic or organic compounds.

In addition, catalysts preferably employed contain no catalytically active amounts of Fe, Ru, Rh, Pd, Os, Ir, Pt, Ag and/or Au and/or their inorganic or organic compounds.

In addition, catalysts preferably employed contain no catalytically active amounts of Zn, In and/or Sn and/or their inorganic or organic compounds.

Various procedures are possible for preparing the catalysts. They can be obtained, for example, by peptizing powdered mixtures of the hydroxides, carbonates, oxides and/or other salts of the components with water and subsequently extruding and annealing (heat-treating) the resulting composition.

However, precipitation methods are generally used to prepare the catalysts according to the invention. Thus, they can be obtained, for example, by joint precipitation of the nickel, cobalt and copper components from an aqueous salt solution containing these elements using mineral bases in the presence of a slurry or suspension of fine-particle powders of an oxygen-containing aluminum, silicon, titanium and/or zirconium compound of low solubility, and subsequently washing, drying and calcining the resulting precipitate. Examples of oxygen-containing aluminum, silicon, titanium and zirconium compounds of low solubility which may be used are aluminum oxide, aluminum oxide hydrate, silicon dioxide, titanium dioxide, zirconium dioxide, zirconium oxide hydrate, zirconium phosphates, borates and silicates.

The catalysts used in the process according to the invention are advantageously prepared by joint precipitation (mixed precipitation) of all their components. This is expediently done by adding an aqueous mineral base, in particular an alkali metal base, for example sodium carbonate, sodium hydroxide, potassium carbonate or potassium hydroxide, to a hot aqueous salt solution containing the catalyst components with stirring until the precipitation is complete. The nature of the salts used is generally not critical: since what principally matters in this procedure is the solubility of the salts in water, one criterion for the preparation of these relatively highly concentrated salt solutions is that they necessarily have good solubility in water. It is regarded as self-evident that, in the selection of the salts of the individual components, of course the anions in the salts chosen will not result in interference, whether by causing unwanted precipitation or by impeding or preventing the precipitation through complex formation.

The precipitates obtained in these precipitation reactions are generally chemically inhomogeneous and consist inter alia of mixtures of the oxides, oxide hydrates, hydroxides, carbonates and insoluble and basic salts of the metals employed. It may prove to be beneficial for the filterability of the precipitates if they are aged, i.e. if they are left alone for some time after the precipitation, where appropriate with heating or passing air through.

The precipitates obtained by these precipitation processes are further processed to the catalysts used in the process according to the invention in a conventional way. After washing, they are generally dried at from 80 to 200° C., preferably from 100 to 150° C., and then calcined. The calcination (heat treatment) is generally carried out at temperatures between 300 and 800° C., preferably at from 400 to 600° C., in particular at from 450 to 550° C.

After the calcination, the catalyst is expediently conditioned, whether by adjusting it to a particular particle size by grinding, or by being ground and then mixed with molding auxiliaries such as graphite or stearic acid, compressed to moldings using a tablet press, and annealed (heat-treated). The annealing temperatures generally correspond to the temperatures for the calcination.

The catalysts prepared in this way contain the catalytically active metals in the form of a mixture of their oxygen-containing compounds, i.e. in particular as oxides and mixed oxides.

The catalysts used in the process according to the invention are preferably prepared by impregnating aluminum oxide ($Al_2O_3$), zirconium dioxide ($ZrO_2$), titanium dioxide ($TiO_2$), silicon dioxide ($SiO_2$) or mixtures of two or more of these carrier materials which are in the form, for example, of powders, chips or shaped articles such as strands, tablets, beads or rings.

Aluminum oxide ($Al_2O_3$) is preferably employed in the form of α-, β-, γ- or θ-$Al_2O_3$ or D10-10 from BASF.

Silicon dioxide ($SiO_2$) is employed, for example, in the form of a silicon dioxide obtained by a precipitation from waterglass or by the sol-gel process, in the form of mesoporous $SiO_2$, silica gel (for example as described in Ullmann, Enzykl. Techn. Chem., 4$^{th}$ edition, Volume 21, pp. 457–63, 1982) or in the form of silicates such as kaolin, hectorite or aluminosilicates or alkali metal or alkaline earth metal aluminosilicates (zeolites), magnesium silicates (for example steatite), zirconium silicates, cerium silicates or calcium silicates.

Zirconium dioxide is employed, for example, in the monoclinic or tetragonal form, preferably in the monoclinic form, and titanium dioxide is employed, for example, as anatase or rutile.

Aluminum oxide is very particularly preferred as carrier material in the catalysts employed in the process according to the invention.

Shaped articles of the abovementioned carrier materials can be produced by conventional processes.

The impregnation of these carrier materials likewise takes place by conventional processes as described, for example, in EP-A-599 180, EP-A-673 918 or A. B. Stiles, Catalyst Manufacture—Laboratory and Commercial Preparations, Marcel Dekker, pages 89 to 91, New York (1983), by application of an appropriate metal salt solution in each case in one or more impregnation stages, the metal salts used being, for example, corresponding nitrates, acetates or chlorides. The composition is dried (heat treatment) and, where appropriate, calcined after the impregnation.

The impregnation can take place by the so-called incipient wetness method in which the oxidic carrier material is moistened with the impregnation solution in accordance with its water-uptake capacity until saturated and no more. However, the impregnation can also take place in supernatant solution.

In multistage impregnation processes it is expedient to dry and, where appropriate, calcine between individual impregnation steps. Multistage impregnation is particularly advantageously applicable when a relatively large amount of metal is to be applied to the carrier material.

For applying a plurality of metal components to the carrier material, the impregnation can take place simultaneously with all the metal salts or in any sequence of the individual metal salts successively.

A special form of impregnation is represented by spray drying, in which the catalyst carrier mentioned is sprayed in a spray dryer with the component(s) to be applied in a suitable solvent. The advantage of this variant is the combination of application and drying of the active component (s) in one step.

The produced catalysts can be stored as such. They are normally reduced by treatment with hydrogen before they are employed according to the invention. However, they can also be employed without this previous reduction, in which case they are reduced by the hydrogen present in the reactor under the conditions of the hydrogenating amination. For the previous reduction, the catalysts are generally exposed to a nitrogen/hydrogen atmosphere initially at from 150 to 200° C. over a period of from 12 to 20 hours and then treated in a hydrogen atmosphere at from 200 to 400° C. for up to about 24 hours. In this previous reduction, at least part of the oxygen-containing metal compounds present in the catalysts is reduced to the corresponding metals so that these are present together with the various oxygen compounds in the active form of the catalyst.

It is possible to employ, for example, the catalysts disclosed in EP-A-382 049, whose catalytically active mass comprises, before the treatment with hydrogen, from 20 to 85% by weight, preferably from 70 to 80% by weight, of $ZrO_2$, from 1 to 30% by weight, preferably from 1 to 10% by weight, of CuO, and in each case from 1 to 40% by weight, preferably from 5 to 20% by weight, of CoO and NiO, for example the catalysts described in loc. cit. on page 6 with the composition 76% by weight Zr, calculated as $ZrO_2$, 4% by weight Cu, calculated as CuO, 10% by weight Co, calculated as CoO, and 10% by weight Ni, calculated as NiO, in the process according to the invention.

It is further possible to employ in the process according to the invention the catalysts disclosed in the earlier European application No. 99111282.2 of Jun. 10, 1999, whose catalytically active mass comprises, before the treatment with hydrogen, from 22 to 40% by weight of $ZrO_2$, from 1 to 30% by weight of oxygen-containing compounds of copper, calculated as CuO, from 15 to 50 by weight of oxygen-containing compounds of nickel, calculated as NiO, where the molar Ni:Cu ratio is greater than 1, from 15 to 50% by weight of oxygen-containing compounds of cobalt, calculated as CoO, from 0 to 10% by weight of oxygen-containing compounds of aluminum and/or manganese, calculated as $Al_2O_3$ and $MnO_2$ respectively, and no oxygen-containing compounds of molybdenum, for example the catalyst A disclosed in loc. cit., page 17, with the composition 33% by weight Zr, calculated as $ZrO_2$, 28% by weight Ni, calculated as NiO, 11% by weight Cu, calculated as CuO and 28% by weight Co, calculated as CoO.

It is possible and preferred to employ in the process according to the invention the catalysts disclosed in EP-A-514 692, whose catalytically active mass comprises, before the treatment with hydrogen, from 5 to 100% by weight of an oxide of copper and nickel in the atomic ratio of from 1:1 to 10:1, preferably from 2:1 to 5:1, and zirconium oxide and/or aluminum oxide, in particular the catalysts disclosed in loc. cit. on page 3, lines 20 to 30, whose catalytically active mass comprises, before the treatment with hydrogen, from 20 to 80, in particular from 40 to 70, % by weight $Al_2O_3$ and/or $ZrO_2$, from 1 to 30% by weight CuO, from 1 to 30% by weight NiO and from 1 to 30% by weight CoO.

It is possible and particularly preferred to employ according to the invention the catalysts disclosed in DE-A-19 53 263 comprising cobalt, nickel and copper and aluminum oxide and/or silicon dioxide with a metal content of from 5 to 80% by weight, in particular from 10 to 30% by weight, based on the complete catalyst, where the catalysts comprise, calculated on the metal content, from 70 to 95% by weight of a mixture of cobalt and nickel and from 5 to 30% by weight of copper, and where the ratio by weight of cobalt to nickel is from 4:1 to 1:4, in particular from 2:1 to 1:2.

The process according to the invention can be carried out batchwise or, preferably, continuously as follows, the catalyst preferably being disposed as fixed bed in the reactor. Flow through the catalyst bed can be either from top to bottom or from bottom to top.

Tubular reactors are particularly suitable for the continuous process.

It has been realized according to the invention that it is particularly advantageous for the selectivity of the reaction if the reaction is carried out in reactors, in particular fixed bed reactors, in which the heat of reaction can be removed particularly efficiently. This makes it possible to set an essentially constant reaction temperature along the reactor.

Thus, in a particularly advantageous embodiment of the process, the conversion of acetone into MIPA is carried out in a tube bundle reactor.

The hydrogenating amination of acetone can be carried out in the liquid phase or in the gas phase.

The reaction is normally carried out at temperatures of from 30 to 300° C., preferably from 50 to 250° C., in particular from 70 to 200° C.

The reaction is generally carried out under an absolute pressure of from 1 to 300 bar (0.1 to 30 MPa). Absolute pressures of from 5 to 250 bar are preferably employed, in particular from 20 to 200 bar.

The use of higher temperatures and a higher total pressure is possible. The total pressure in the reaction vessel, which derives from the total of the partial pressures of ammonia, of acetone, of the products formed in the reaction and of the solvent which is also used where appropriate at the stated temperatures, is expediently adjusted to the required reaction pressure by injecting hydrogen. It is possible in this connection to use a mixture of hydrogen and an inert gas, such as, for example, nitrogen, in place of pure hydrogen.

The hydrogen is generally fed into the reaction in an amount of from 5 to 400 l (S.T.P.), preferably in an amount of from 50 to 200 l (S.T.P.), per mole of acetone, the liter data having been converted in each case to standard conditions (S.T.P.).

The reaction preferably takes place without additional solvent. However, it is possible also to use a solvent which is inert under the reaction conditions, such as methanol, ethanol, propanol, tetrahydrofuran, dioxane, N-methylpyrrolidone, Mihagol or ethylene glycol dimethyl ether.

It may be advantageous for the selectivity of the reaction, depending on the composition of the catalyst used according to the invention, to mix the catalyst shaped articles in the reactor with inert packings in order, as it were, to dilute them. The proportion of packings in such catalyst preparations can be from 20 to 80, particularly preferably from 30 to 60 and, in particular, from 40 to 50 parts by volume.

The procedure in practice is generally to feed the acetone and the ammonia simultaneously into the catalyst, which is preferably present in a tube bundle reactor, at the required reaction temperature and the required pressure. The molar ratio of acetone to ammonia is generally from 1:1 to 1:250, preferably from 1:1 to 1:50, particularly preferably from 1:1.2 to 1:10. The space velocity in this case is generally from 0.05 to 5, preferably from 0.05 to 2, kg of acetone per liter of catalyst (bulk volume) and per hour. It is expedient in this case for the reactants to be heated even before being fed into the reaction vessel.

The reactants can be passed either upward or else downward through the reactor. Excess ammonia can be recycled together with the hydrogen.

After expediently decompressing the discharge from the reaction, the ammonia and the hydrogen are removed therefrom, and the resulting MIPA is purified by distillation. Recovered ammonia and hydrogen are advantageously returned to the reaction zone. The same applies to any incompletely reacted acetone or isopropanol produced by hydrogenation. It is also possible to return part of the total discharge from the reactor.

The water formed during the reaction generally has no adverse effect on the degree of conversion, the reaction rate, the selectivity and the catalyst service life and is therefore expediently removed from the reaction product only when it is worked up by distillation.

EXAMPLES

A) Preparation of catalyst A (according to DE-A-19 53 263)

Aluminum oxide extrudates with a strand diameter of 4 mm were covered with a solution containing 5% by weight of each of Co and Ni and 2% by weight of Cu (calculated as metal). This was a solution of the metal nitrates.

After an impregnation time of about 15 minutes, the strands were dried at 120° C. and then annealed at 520° C.

The impregnation/drying/annealing was then repeated.

The resulting catalyst A had the composition:

76% by weight of $Al_2O_3$, 4% by weight of copper oxide, calculated as CuO, 10% by weight of CoO and 10% by weight of NiO.

B) Reaction examples 1 to 12:

To carry out the tests continuously, a high-pressure reactor with an internal diameter of 45 mm and a length of 350 cm was used. A thermoelement with a diameter of 12 mm was attached in the middle of the reactor in the axial direction. The reactor was packed in the lower part with 700 ml of stainless steel Pall rings, on top of this 3500 ml=3509 g of catalyst A in strand form were introduced, and a further 700 ml of stainless steel Pall rings were introduced as top layer. Acetone, ammonia and hydrogen were fed into the reactor from top to bottom. The reactor pressure was adjusted by supplying hydrogen. Downstream of the reactor, the reaction mixture was cooled, decompressed to atmospheric pressure and analyzed.

The detailed test conditions and the results are to be found in the following table:

| T No. | p bar | T ° C. | SV kg/(l*h) | MR $NH_3$/Ac. | MIPA % (*) | DIPA(*) % (*) | Acetone % (*) | iPrOH % (*) | Others % (*) |
|---|---|---|---|---|---|---|---|---|---|
| 1 | 200 | 150 | 0.1 | 7.8 | 98.9 | 0.05 | 0.01 | 0.9 | 0.1 |
| 2 | 200 | 130 | 0.35 | 2.1 | 96.8 | 0.7 | 0 | 2.2 | 0.3 |
| 3 | 65 | 135 | 0.1 | 4.6 | 97.5 | 0.05 | 0 | 2.1 | 0.3 |
| 4 | 50 | 130 | 0.1 | 6.0 | 97.0 | 0.2 | 0 | 2.2 | 0.6 |
| 5 | 50 | 130 | 0.2 | 3.0 | 97.4 | 0.1 | 0 | 1.7 | 0.8 |
| 6 | 50 | 150 | 0.35 | 2.1 | 97.5 | 0.1 | 0.2 | 1.2 | 0.8 |
| 7 | 50 | 160 | 0.35 | 2.1 | 97.3 | 0.2 | 0.02 | 1.8 | 0.6 |
| 8 | 40 | 135 | 0.1 | 4.6 | 97.5 | 0.05 | 0 | 2.1 | 0.3 |
| 9 | 40 | 140 | 0.2 | 4.6 | 98.1 | 0.02 | 0 | 1.6 | 0.3 |

-continued

| T No. | p bar | T °C | SV kg/(1*h) | MR NH₃/Ac. | MIPA % (*) | DIPA(*) % (*) | Acetone % (*) | iPrOH % (*) | Others % (*) |
|---|---|---|---|---|---|---|---|---|---|
| 10 | 40 | 140 | 0.4 | 4.6 | 97.8 | 0.02 | 0.3 | 1.3 | 0.4 |
| 11 | 35 | 140 | 0.35 | 2.1 | 97.1 | 0.15 | 0.15 | 1.5 | 1.0 |
| 12 | 35 | 120 | 0.35 | 2.1 | 96.8 | 0.15 | 0.5 | 1.2 | 1.0 |

SV = space velocity in kg of acetone per 1 of catalyst (bulk volume) and per hour
MR = molar ratio
Ac. = acetone
DIPA = diisopropylamine
iPrOH = isopropanol
Others = other byproducts
(*) GC column: 30 m Stabilwax DB Amine, 0.25 μm internal diameter, 0.5 μm film thickness, Temperature program: 50° C. for 10 min., to 150° C. at 4° C./min.

Carrier gas: nitrogen

GC evaluation: Corrected percentage areas for MIPA, DIPA and isopropanol were found by previously determining the GC factors for DIPA and iPrOH in relation to MIPA (factor 1) using a MIPA+DIPA+iPrOH test mixture.

We claim:

1. A process for preparing monoisopropylamine by reacting acetone with ammonia and with hydrogen at elevated temperature and elevated pressure in the presence of a catalyst, wherein the catalytically active mass of the catalyst comprises, after its preparation and before the treatment with hydrogen, from 40 to 85% by weight of aluminum oxide ($Al_2O_3$), from 1 to 25% by weight of oxygen-containing compounds of copper, calculated as CuO, from 5 to 40% by weight of oxygen-containing compounds of nickel, calculated as NiO, and from 5 to 40% by weight of oxygen-containing compounds of cobalt, calculated as CoO.

2. A process as claimed in claim 1, wherein the catalytically active mass of the catalyst comprises, after its preparation and before the treatment with hydrogen, from 50 to 85% by weight of aluminum oxide ($Al_2O_3$), from 1 to 15% by weight of oxygen-containing compounds of copper, calculated as CuO, from 5 to 25% by weight of oxygen-containing compounds of nickel, calculated as NiO, and from 5 to 25% by weight of oxygen-containing compounds of cobalt, calculated as CoO.

3. A process as claimed in claim 1, wherein the reaction is carried out under absolute pressures of from 1 to 300 bar.

4. A process as claimed in claim 1, wherein the reaction is carried out at temperatures of from 30 to 300° C.

5. A process as claimed in claim 1, wherein the catalyst is employed in the form of shaped articles.

6. A process as claimed in claim 1, wherein the reaction is carried out in a tube bundle reactor.

7. The process of claim 1, wherein the reaction is carried out in a reactor in which a part of the total discharge from the reactor is returned to the reactor.

8. The process of claim 1, wherein the reaction is carried out in the gas phase.

9. The process of claim 1, wherein the reaction is carried out under absolute pressures of from 20 to 200 bar and at temperatures from 70 to 200° C.

* * * * *